US006368554B1

(12) United States Patent
Wajsfelner et al.

(10) Patent No.: US 6,368,554 B1
(45) Date of Patent: Apr. 9, 2002

(54) METHOD FOR STRIPPING AND SANITIZING A CONTAINER INNER SURFACE AND IMPLEMENTING DEVICE

(75) Inventors: René Wajsfelner, 3, Place de l'Eglise, F-94260 Fresnes; Jacques Depoizier, Saint Julien de Beychevelle; Jean-Paul Longuemard, Villebon, all of (FR)

(73) Assignees: Rene Wajsfelner, Fresnes; Societe Civile Chateau Leoville las Cases, Saint Julien de Beychevelle, both of (FR)

( * ) Notice: Subject to any disclaimer, the term of this patent is extended or adjusted under 35 U.S.C. 154(b) by 0 days.

(21) Appl. No.: 09/720,316

(22) PCT Filed: Jun. 9, 1999

(86) PCT No.: PCT/FR99/01363

§ 371 Date: Mar. 1, 2001

§ 102(e) Date: Mar. 1, 2001

(87) PCT Pub. No.: WO00/00305

PCT Pub. Date: Jan. 6, 2000

(30) Foreign Application Priority Data

Jun. 26, 1998 (FR) ............................................ 98 08140

(51) Int. Cl.[7] .................................................. A61L 2/00

(52) U.S. Cl. ............................ 422/22; 422/22; 422/24; 422/27; 422/28; 422/30; 250/453.11; 250/454.11; 250/455.11

(58) Field of Search ....................... 250/453.11, 454.11, 250/455.11; 422/22, 24, 28, 27, 30

(56) References Cited

U.S. PATENT DOCUMENTS 4,867,796 A 9/1989 Asmus et al. .................. 131/1
4,920,994 A * 5/1990 Nachbar ........................ 134/1
5,531,856 A * 7/1996 Engelsberg et al. .... 219/121.68

FOREIGN PATENT DOCUMENTS

DE 43 20 341 12/1994
EP 0 520 847 12/1992
GB 2206605 A * 1/1989
GB 2 316 528 2/1998

* cited by examiner

*Primary Examiner*—Robert J. Warden, Sr.
*Assistant Examiner*—Imad Soubra
(74) *Attorney, Agent, or Firm*—Young & Thompson

(57) ABSTRACT

A plused radiation produced by an intense optical source is applied to the inner surface of a wooden container having a surface layer of organic and/or mineral deposit. Each pulse is of sufficiently short duration having sufficiently high treating energy density per unit area to bring about sublimation of the surface layer. The resulting exposed container surface is sanitized by the heat released by the radiation.

25 Claims, 1 Drawing Sheet

METHOD FOR STRIPPING AND SANITIZING A CONTAINER INNER SURFACE AND IMPLEMENTING DEVICE

FIELD OF THE INVENTION

The present invention relates to a process for stripping and sterilizing the internal surface of a container, for example made of wood, metal, concrete or any other material, especially a wooden cask having a surface layer of a coating of organic and/or mineral material, especially a coating of tannin resulting from the maturation of a wine in a cask, as well as to a device for its implementation.

Wooden casks will be of particular interest in the remainder of the description, but it should be well understood that the invention is in no way limited thereto and that it can be applied to any type of container, whatever it is made of.

BACKGROUND OF THE INVENTION

During the period of maturing wines in a barrel, it is generally accepted that the wood transfers various substances, such as furans, lactones, aldehydes, phenolic acids, phenols and ketones to the wine. The barrel puts the wine in an oxidizing balance and acts as a kind of micro-doser of oxygen, which allows a first oxidation-reduction aging of the wine. It is generally assumed that a new barrel transfers tannic substances to the wine while an old barrel transfers substances from the decomposition of the wood. A one-year-old barrel, i.e. a barrel having already served to mature a wine for one year, generally gives a taste of pure wood to the wine, while a six-year-old barrel generally gives a rancid taste.

To mature certain wines, wooden barrels, the inside of which has been scorched on the surface, are also used to transfer other substances, such as phenolic compounds, furanic aldehydes and color, to the wine.

Usually a barrel may serve to mature up to four wines over a period of 4 to 6 years. After this period, the barrel can no longer serve as a maturing tool since the wine has penetrated by about 5 to 10 mm into the thickness of the barrel which has a thickness of about 22 to 27 mm, this penetration of the wine causing sealing of the wood pores by the tannin coatings and by the alterations in the compounds of the wood, such as the phenolic compounds, tartaric acid, etc., which prevents the subsequent transfers of substances between the wood and the wine, which transfers are essential to the maturation of the wine. These old barrels may still serve as storage containers, but this is not usually the case, since microbe-related accidents may arise during storage, between the wine and the coatings covering the internal surface of the barrel.

For the maturation barrels, the quality of the wood used is very important and, in French vineyards, the wood used generally comes from oaks of about 150 to 300 years of age, which therefore have a very long renewal time faced with a very greatly increasing recent demand.

In order to reduce the cost of the barrels and to save the limited national heritage in oaks, a process for renovating the barrel has already been proposed.

One solution consists in carrying out a mechanical stripping, using a plane or a sander, inside the barrel, then in possibly carrying out scorching, in order to regain the organoleptic nature which is characteristic of a new barrel. However, this solution is lengthy and expensive to implement and does not allow the barrel to be sterilized against microbial infections. Furthermore, such a mechanical stripping leads to removing an appreciable thickness, several millimeters, of the barrel, which limits the number of possible renovations.

Another solution consists in chemically cleaning the barrel, but this solution is very cumbersome to implement and expensive.

Furthermore, the current renovation processes give quite disappointing results for the quality of the wines, since stripping which is too intense leads to a "plank" taste by completely renovating the raw wood, while stripping which is too light has no effect.

Furthermore, during the renovation of the barrel, it is difficult to reproduce the initial traditional scorching, since when the barrel is too scorched, it develops strange characteristics.

SUMMARY OF THE INVENTION

The object of the invention is to propose a process for stripping and sterilizing the internal surface of a container, which is both simple to implement and which allows a very high number of renovations.

The invention is based on the principle of renovation by laser which ensures accurate and selective stripping at a controlled temperature, by photoremoval of the biological stains, for example fungal, mold, polychlorophenol and chloroanisole compounds, and/or mineral stains which are deposited over the internal surface of the container. Since the biological stains have physical characteristics which are different to those of the material forming the container, the heat increase during the absorption of the light produced by the laser will be faster in the coating of organic and/or mineral material than in the container, which makes it possible to remove the biological and/or mineral stains without causing a transfer of energy to within the material forming the cask.

For this purpose, the subject of the invention is a process for stripping and sterilizing the internal surface of a container made of wood, metal, concrete or some other material, having a surface layer of a coating of organic and/or mineral material, especially a coating of tannin resulting from the maturation of a wine in a cask, characterized in that it consists in applying, over the surface to be treated, pulsed radiation produced by an intense optical source, each pulse having a duration which is short enough and an energy density per unit area to be treated which is high enough to cause the sublimation of the said surface layer, the surface of the container thus stripped being sterilized by the heat released by the radiation. Using the invention, the layer of organic and/or mineral material is sublimed, which generates a gaseous plasma in the form of smoke, which avoids the drawbacks connected with the use of an aqueous solution.

Advantageously, each pulse has a duration of between 10 and 200 ns and an energy density of between about 6.5 and 9 $J/cm^2$. Preferably, each pulse has a duration of about 100 ns and an energy density of about 8 $J/cm^2$.

A long pulse duration, for example of the order of ms or us, would lead to a transfer of energy into the material forming the container and a low rate of ejection of the sublimed marks, while the organic and/or mineral coatings have to be removed over a small thickness, quickly and without consuming too much energy. With a. pulse duration of about 100 ns a very high peak value is obtained for the beam, which causes a high ejection rate of the sublime organic and/or mineral material and low diffusion of the heat into the material forming the container.

According to another characteristic, the process consists in applying, over each unit area, from 2 to 20 pulses, preferably between 4 and 10 pulses, depending on the type of material of the container to be treated, the state of the surface to be treated and the thickness of the organic and/or mineral coating.

According to another characteristic, the radiation is determined so as to cause a quasi-adiabatic sublimation of the layer of organic and/or mineral material on the surface to be treated. In particular, provision can be made for 80% of the heat produced by the radiation to be absorbed by the surface layer during sublimation, the remaining 20% being dissipated within the thickness of the material forming the container.

Preferably, each pulse causes the sublimation of about 20 $\mu$m thickness of material surface to be treated.

Advantageously, the process consists in evacuating the gaseous plasma produced during the sublimation, by sucking it up or blowing it out using an inert gas or air.

According to another characteristic, the intense optical source is a laser source, for example a $CO_2$ laser source at atmospheric pressure and with transverse excitation.

According to another aspect of the invention, for a wooden container, the process consists, simultaneously with or subsequent to the step of stripping and sterilizing, in applying over the surface to be treated a second intense optical radiation, the said second radiation being applied continuously or quasi-continuously for a duration which is long enough and with an energy density per unit area to be treated which is high enough to cause scorching of the wood on the surface. Advantageously this second radiation is applied by a laser source with a defocused beam or by beam scanning.

Preferably, the second radiation has a power density of between 100 and 200 W/cm$^2$ for a duration of application of about 0.5 to 0.2 seconds. In this case, the second radiation preferably has an energy density per unit area to be treated of about 20 J/cm$^2$.

Although the energy density received by the wood, in the case of scorching or toasting, is greater than that for stripping, the total energy is transferred over a long time during scorching, which means that the heat diffuses into the wood and chars it on the surface, while, in the case of stripping, the energy is applied over a very short time, causing instant sublimation of the organic layer.

In another variant, the second radiation is applied by an infrared or ultraviolet lamp, for example, a lamp having a power of 70 W for an application time of several minutes, with a distance of a few centimeters between the radiation source and the surface to be treated.

The subject of the invention is also a device for implementing the aforementioned process, characterized in that it comprises an intense optical source capable of producing pulsed radiation in order to strip and sterilize the internal surface of the container, a waveguide connected to the optical output of the source, an optical focusing head connected to the output of the waveguide, in order to define the cross section of interaction with the surface to be treated and thus the energy density to deposit per unit area, a robot for the relative movement between the optical head and the internal surface of the container to be treated, and a central control unit in order to control and synthesize, on the one hand, the source parameters such as the number of pulses to be applied per unit area, the impulse frequency and the radiation power of the source, and on the other hand, the movements to be carried out by the robot in order to treat the entire internal surface of the container.

Advantageously, the robot is capable of making the said optical head pivot through an angle of about 120° with respect to the axis of the container.

According to another characteristic, the robot is capable of driving the optical head in relative rotation about the axis of the container with respect to the container.

According to yet another characteristic, the robot is capable in driving the container in relative axial translation with respect to the optical head, which may in this case be connected to a telescopic or extensible waveguide.

Preferably, the optical head is located at a distance from the surface to be treated of about a few tens of centimeters.

According to another aspect of the invention, the device comprises a camera for displaying the surface treatment, the said camera being connected to a display screen and to the central control unit in order to control the surface treatment visually and in real time.

According to another characteristic, the optical head is arranged so as to penetrate inside the container, for example by the bunghole of a cask made of wood, or by a hole specially made in one of the heading pieces of the cask or else by one of the ends of the cask from which the heading piece has been removed.

Advantageously, the device comprises a pipe for sucking up or blowing out smoke generated by the stripping.

The purpose of removing the gaseous plasma is to avoid, on the one hand, any recontamination of the treated surface and surroundings, on the other hand, any interference with the optical beam and with any display camera.

According to another characteristic, the device a second intense optical source for producing the second radiation for scorching a container made of wood.

BRIEF DESCRIPTION OF THE DRAWINGS

In order to better understand the object of the invention, several embodiments shown on the appended drawing will now be described, by way of purely illustrative and non-limiting examples.

In this drawing.

DETAILED DESCRIPTION OF THE INVENTION

Figure 1:
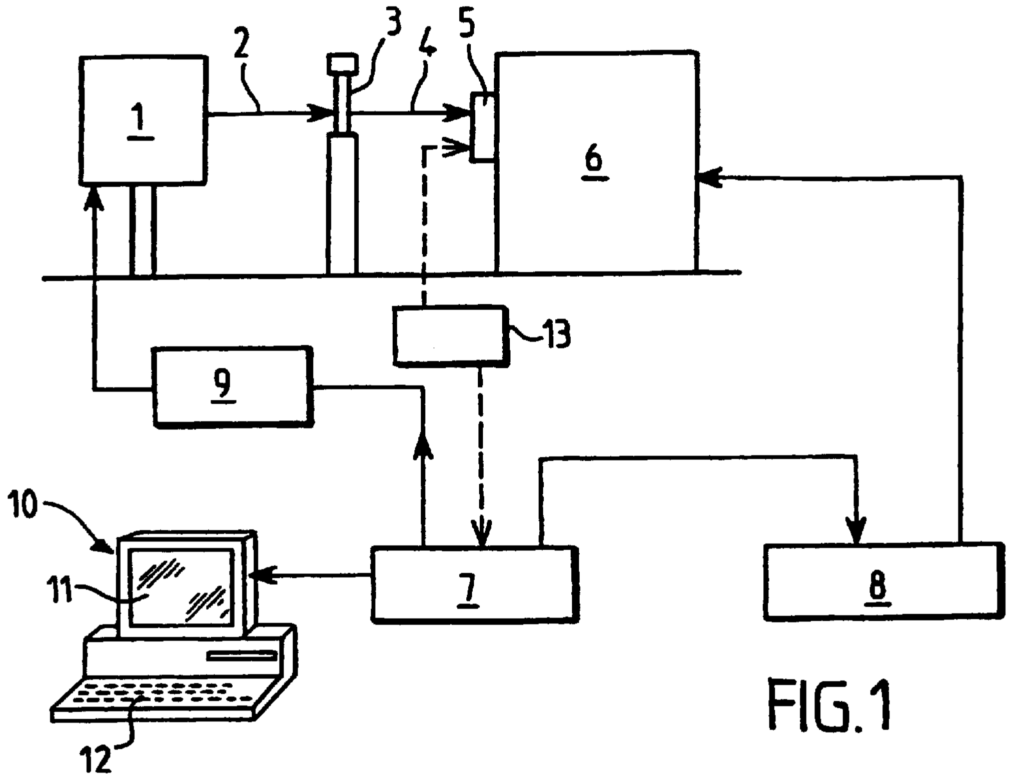
FIG. 1 is a block diagram of the device of the invention adapted for a test on a sample.

In FIG. 1, a laser source 1 is shown which is intended to produce a laser beam 2 in the direction of a convergent lens 3 which causes a beam 4 to converge on a stave 5 of a wooden cask. The stave 5 is held by a robot 6. A central control unit 7 is connected by a robot control interface 8 to the robot 6, and by a synchronization interface 9 to the laser source 1. The central control unit 7 is combined with a periphery unit 10 formed by a screen 11 and a keyboard 12. A camera 13 may also be connected to the central control unit 7, as shown by dashed lines, in order to display the treatment of the surface of the stave 5. Although the apparatus illustrated in FIG. 1 is adapted to carry out tests on a sample 5, the general principle of the invention remains substantially the same.

Figure 2:
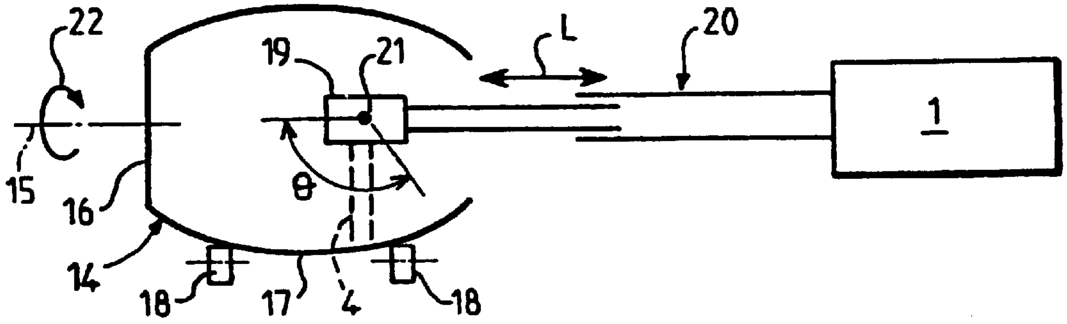
FIG. 2 is a simplified partial diagram of the device of the invention for stripping a cask.

FIG. 2 shows a wooden barrel 14, bulging in the middle, made in a known manner from staves which are assembled and hooped, one of the ends of which is closed by a circular heading piece 16 and the other end of which is open in the direction of the laser source 1. The barrel 14 rests by the external convex surface of its side wall 17 on rotating rollers 18 which are intended to be rotated about an axis parallel to the axis 15 of the barrel 14, by the aforementioned robot 6.

The aforementioned convergent lens 3 is included in an optical focusing head 19 which is connected to the laser source 1 by a waveguide 20 which in this case is telescopic in the axial direction indicated by the double arrow L, but which, as a variant, could be extensible. The waveguide 20 is substantially aligned with the axis 15 of the barrel 14. The optical head 19 is articulated with respect to the waveguide 20, about a horizontal axis 21 which is perpendicular to the axis 15 of the barrel. The optical head 19 is designed to pivot about this axis 21 through an angle $\theta$ of about 120°, such that the convergent beam 4 exiting from the optical head 19 is able to pivot between a position (not shown) where the said beam 4 is aligned with the axis 15 of the barrel in the direction of the heading piece 16, and a position inclined by 30° with respect to the vertical, in the direction of the open end of the barrel. Thus the optical head 19 can scan the entire internal surface of the barrel, that is the internal surface of the heading piece 16 and the internal concave surface of the side walls 17 of the barrel.

The rotating rollers 18 allow the barrel 14 to be turned about its axis 15, as shown by the arrow 22. Of course, as a variant, the waveguide 20 could be designed to rotate axially, instead of rotating the barrel 14.

Figure 3:
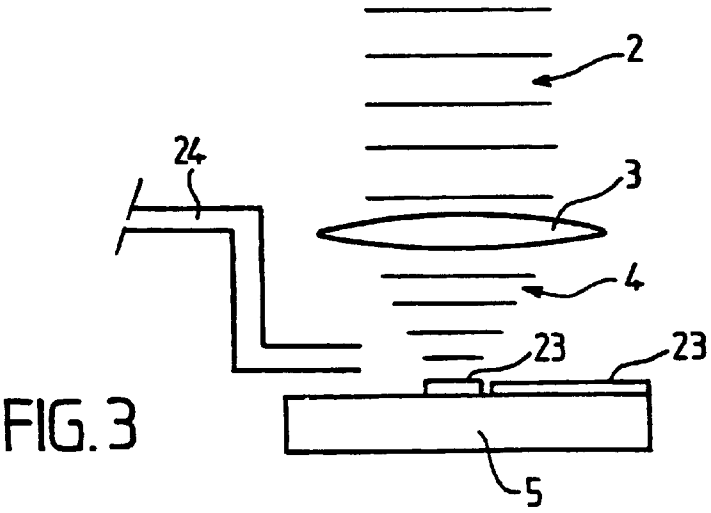
FIG. 3 is an enlarged view of a detail of FIG. 1, showing the stripping region.

FIG. 3 shows that the beam 2 coming from the optical source 1 is converted into a convergent beam 4 by the lens 3, in order to make this beam converge on a region of predetermined limited area of the internal wall of the stave 5, in order to sublimate a layer of organic material coating 23. The smoke produced by the sublimation of the layer of organic material 23 may be sucked up or blown out via a pipe 24 inserted in the barrel 14, preferably close to the region of treatment of a stave 5.

The pipe for sucking up or blowing out the smoke 24 may be combined with the camera 13. The camera 13 is, preferably, provided with an autofocus objective lens, making it possible to view the surface to be treated on the control screen 11, and therefore for the operator to control, without risk, the quality of the stripping and of the scorching.

Using the combined movements of the waveguide in the axial direction of the barrel, of the axial rotation of the barrel 14 and of the limited angular pivoting of the optical head 19, the entire internal surface of the barrel can be treated.

Stripping Step

In the course of the stripping tests which were carried out, it was found that, with a pulsed laser beam having an energy density of 2 J over a surface to be treated of 24 $mm^2$, i.e. an energy density of 8 $J/cm^2$ which corresponds to a power density of 80 $MW/cm^2$ for a pulse duration of 100 ns, each pulse causes the removal of 20 $\mu$m thickness of wood, which is negligible with respect to the thickness of a stave which is generally between 22 and 27 mm. This is because the coating of organic material is generally intimately linked to a surface layer of the internal surface of the wood, which, during stripping, causes the removal of the organic material and of a layer of wood of a corresponding thickness, which layer is impregnated by the said layer of organic material.

The laser source is preferably a $CO_2$ laser at atmospheric pressure and operating with transverse excitation (TEA), having a wavelength of 10.6 $\mu$m, with a beam output cross section of 16×32 mm.

Preferably, the focusing head will have a long focal length with respect to the distance between the said head and the surface to be treated, so as to reduce the accuracy of positioning the head with respect to the cross section for interaction of the beam with the surface to be treated. The distance between the optical head 19 and the surface to be treated may vary between 30 and 50 cm.

To industrialize the process, several laser sources, for example three sources, could be coupled in parallel, each one having a pulse frequency of 200 Hz, in order to alternately deliver energy over a same optical path, which makes it possible to obtain an overall pulse frequency of 600 Hz, each pulse having, for example, an energy density of between 150 and 200 $mJ/cm^2$, the rate of displacement of the laser beam with respect to the surface to be treated being determined by the central control unit which comprises a computer, so as to obtain an energy density of 8 $J/cm^2$ over the surface to be treated.

Scorching Step

To scorch the wood, three different solutions were tested:

with a $CO_2$ laser source having a power of 3 kW and generating an out-of-focus beam having a power density of 180 $W/cm^2$, the exposure time needed is greater than 50 ms;

with a $CO_2$ laser source having a power of 10 W and generating a scanning beam having a power density of about 10 $W/cm^2$, the distance between the focusing head and the surface to be treated being about 60 cm, the exposure time needed is markedly longer, about 5 mn, in order to obtain the desired scorching, but in this case, the scorching affects a depth of the order of mm and the quantity of energy deposited is much greater;

with an infrared lamp of 1 $\mu$m wavelength, having a power of 80 W and a beam aperture angle of 28°, at a distance of about 3 cm from the surface to be treated, the exposure time needed is markedly longer at about 9 mn.

These three scorching solutions are not illustrated in the drawing, but they could be mounted on the robot so as to couple the intense optical source for scorching and the laser source for stripping. A single double-beam optical source could also be provided, producing simultaneously or successively pulsed radiation for stripping and continuous radiation for scorching. These two radiations can be produced simultaneously since their characteristics of interaction with the surface to be treated are markedly different, which avoids any interference.

For the stripping, the number of pulses per unit area, the duration of each pulse and the energy density per unit area, will be able to be determined as a function of the surface state, the quality of the wood and the thickness of the layer to be removed.

For the scorching, the exposure time and the power density of the intense optical source will be determined as a function of the degree of scorching desired by the user.

Although the invention has been described in connection with several particular embodiments, it is clearly obvious that the invention is in no way limited to them and that it comprises all the technical equivalents of the means described as well as their combinations if these come within the scope of the invention.

We claim:

1. A process for stripping and sterilizing the internal surface of a wooden container, having a surface layer of a coating of organic and/or mineral material, comprising:

applying a pulsed radiation produced by an infrared optical source over the internal surface, each pulse having a duration and an energy density per unit area to be treated to cause sublimation of the surface layer, the surface of the wood thus stripped being sterilized by the heat released by the radiation, wherein each pulse has a duration of about 100 ns and an energy density of about 8 J/cm$^2$.

2. The process according to claim 1, further comprising evacuating gaseous plasma produced during the sublimation, by sucking up or blowing out using an inert gas or air.

3. The process according to claim 1, wherein the optical source comprises a laser source.

4. The process according to claim 3, wherein the optical source comprises a laser source.

5. A process for stripping and sterilizing the internal surface of a wooden container, having a surface layer of a coating of organic and/or mineral material, comprising:

applying a pulsed radiation produced by an infrared optical source over the internal surface, each pulse having a duration and an energy density per unit area to be treated to cause sublimation of the surface layer, the surface of the wood thus stripped being sterilized by the heat released by the radiation, wherein the radiation is determined so as to cause a quasi-adiabatic sublimation of the layer of organic and/or mineral material and wherein 80% of the heat produced by the radiation is absorbed by the surface layer during the sublimation, the remaining 20% being dissipated within the thickness of the wood.

6. The process according to claim 5, further comprising evacuating gaseous plasma produced during the sublimation, by sucking up or blowing out using an inert gas or air.

7. A process for stripping and sterilizing the internal surface of a wooden container, having a surface layer of a coating of organic and/or mineral material, comprising:

applying a pulsed radiation produced by an infrared optical source over the internal surface, each pulse having a duration and an energy density per unit area to be treated to cause sublimation of the surface layer, the surface of the wood thus stripped being sterilized by the heat released by the radiation, wherein each pulse causes the sublimation of about 20$\mu$m thickness of material.

8. The process according to claim 7, further comprising evacuating gaseous plasma produced during the sublimation, by sucking up or blowing out using an inert gas or air.

9. The process according to claim 7, wherein the optical source comprises a laser source.

10. A process for stripping and sterilizing the internal surface of a wooden container, having a surface layer of a coating of organic and/or mineral material, comprising:

applying a pulsed radiation produced by an infrared optical source over the internal surface, each pulse having a duration and an energy density per unit area to be treated to cause sublimation of the surface layer, the surface of the wood thus stripped being sterilized by the heat released by the radiation; and simultaneously with or subsequent to the step of stripping and sterilizing, applying over the internal surface a second optical radiation, the second radiation being applied continuously or quasi-continuously for a duration and with an energy density per unit area to be treated to cause scorching of the wood on the surface, wherein the second radiation has a power density of between 100 and 200 W/cm$^2$ for a duration of application of about 0.05 to 0.2 seconds.

11. The process according to claim 10, wherein the second radiation is applied by a laser source with an out-of-focus beam or by beam scanning.

12. The process according to claim 10, wherein the second radiation is applied by an infrared or ultraviolet lamp.

13. A process for stripping and sterilizing the internal surface of a wooden container, having a surface layer of a coating of organic and/or mineral material, comprising:

applying a pulsed radiation produced by an infrared optical source over the internal surface, each pulse having a duration and an energy density per unit area to be treated to cause sublimation of the surface layer, the surface of the wood thus stripped being sterilized by the heat released by the radiation; and simultaneously with or subsequent to the step of stripping and sterilizing, applying over the internal surface a second optical radiation, the second radiation being applied continuously or quasi-continuously for a duration and with an energy density per unit area to be treated to cause scorching of the wood on the surface, wherein the second radiation has an energy density per unit area to be treated of about 20 J/cm$^2$.

14. The process according to claim 13, wherein the second radiation is applied by a laser source with an out-of-focus beam or by beam scanning.

15. The process according to claim 13, wherein the second radiation is applied by an infrared or ultraviolet lamp.

16. A device for stripping and sterilizing the internal surface of a wooden container having a surface layer of a coating of organic and/or mineral material, comprising:

an optical source capable of producing pulsed radiation;

a waveguide connected to the optical output of the source;

an optical focusing head connected to the output of the waveguide, in order to define the cross section of interaction with the surface to be treated and thus the energy density to deposit per unit area;

a robot for the relative movement between the optical head and the internal surface of the container to be treated, wherein the source is an infrared optical source, each pulse of which has a duration of between 10 and 200 ns and an energy density of between 6.5 and 9 J/cm$^2$ for the stripping and the sterilization of the internal surface of a wooden container and further comprising a central control unit to control and synthesize the source parameters and the movements to be carried out by the robot in order to treat the entire internal surface of the container, wherein the robot is capable of making the optical head pivot through an angle of about 120° with respect to the axis of the container, of driving the optical head in relative rotation about the axis of the container with respect to the container, and in driving the container in relative axial translation with respect to the optical head.

17. The device according to claim 16, further comprising a camera for displaying the surface treatment, the camera being connected to a display screen and to the central control unit in order to control the surface treatment visually and in real time.

18. The device according to claim 16, further comprising a pipe for sucking up or blowing out smoke generated by the stripping.

19. The device according to claim 16, further comprising a second optical source for producing a second radiation for scorching a container made of wood.

20. The device according to claim 16, wherein the optical source parameters comprise the number of pulses to be applied per unit area, the impulse frequency and the radiation power of the source.

21. A device for stripping and sterilizing the internal surface of a wooden container having a surface layer of a coating of organic and/or mineral material, comprising:

an optical source capable of producing pulsed radiation;

a waveguide connected to the optical output of the source;

an optical focusing head connected to the output of the waveguide, in order to define the cross section of interaction with the surface to be treated and thus the energy density to deposit per unit area;

a robot for the relative movement between the optical head and the internal surface of the container to be treated, wherein the source is an infrared optical source, each pulse of which has a duration of between 10 and 200 ns and an energy density of between 6.5 and 9 J/cm$^2$ for the stripping and the sterilization of the internal surface of a wooden container and further comprising a central control unit to control and synthesize the optical source parameters and the movements to be carried out by the robot in order to treat the entire internal surface of the container, wherein the optical head is arranged so as to penetrate inside the container by way of a bunghole of a cask made of wood, a hole specifically made in a heading piece of a cask made of wood or by one end of a cask of wood from which a heading piece has been removed.

22. The device according to claim 21, further comprising a camera for displaying the surface treatment, the camera being connected to a display screen and to the central control unit in order to control the surface treatment visually and in real time.

23. The device according to claim 21, further comprising a pipe for sucking up or blowing out smoke generated by the stripping.

24. The device according to claim 21, further comprising a second optical source for producing a second radiation for scorching a container made of wood.

25. The device according to claim 21, wherein the optical source parameters comprise the number of pulses to be applied per unit area, the impulse frequency and the radiation power of the source.

* * * * *